(12) United States Patent
Shaeef

(10) Patent No.: US 6,239,445 B1
(45) Date of Patent: May 29, 2001

(54) OPTICAL INSPECTION APPARATUS WITH REMOVABLE INSERTS

(75) Inventor: Nazeer Shaeef, Mishawaka, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/259,599

(22) Filed: Mar. 1, 1999

(51) Int. Cl.[7] ............................. G01N 21/49; G01N 21/00

(52) U.S. Cl. ........................ 250/576; 250/573; 356/440; 422/58; 422/104

(58) Field of Search ........................... 250/573, 574, 250/576, 222.1, 216; 356/39, 402, 440, 446; 422/56, 58, 63, 82.05, 104

(56) References Cited

U.S. PATENT DOCUMENTS

| | | | |
|---|---|---|---|
| 3,907,503 | 9/1975 | Betts et al. | 422/67 |
| 4,689,202 | 8/1987 | Khoja et al. | 422/65 |
| 5,059,394 | 10/1991 | Phillips et al. | 422/68.1 |
| 5,231,576 | 7/1993 | Suzuki et al. | 356/39 |
| 5,661,563 | 8/1997 | Howard et al. | 356/446 |
| 5,945,341 | * 8/1999 | Howard, III | 422/58 |

OTHER PUBLICATIONS

Clinitek 50 User's Guide, 1996 Bayer Corporation, Revised Mar. 1996, 18 pages.
Howard, W. E. III, An Introduction to Reflectance Spectroscopy for Dry Phase Reagent Chemistry, *Miles Science Journal*, pp. 33–37.

* cited by examiner

Primary Examiner—John R. Lee
Assistant Examiner—Kevin Pyo
(74) Attorney, Agent, or Firm—Jerome L. Jeffers

(57) ABSTRACT

An apparatus in accordance with the invention is directed to an optical inspection apparatus (10) adapted to inspect a liquid sample. The apparatus includes a tray (20) that is adapted to be physically coupled to a first liquid sample carrier (22) and a second liquid sample carrier (40), each of the first and second liquid sample carriers (22, 40) being adapted to hold a liquid sample. The first liquid sample carrier (22) is of a first type and the second liquid sample carrier (40) is of a second type different from the first type. The apparatus (10) has a light source (108) adapted to illuminate one of the liquid samples associated with one of the liquid sample carriers (22 or 40) when the liquid sample carrier (22 or 40) is coupled to the tray (20) at an inspection location and a detector (110) adapted to receive light from the liquid sample when the liquid sample is being illuminated by the light source (108).

17 Claims, 3 Drawing Sheets

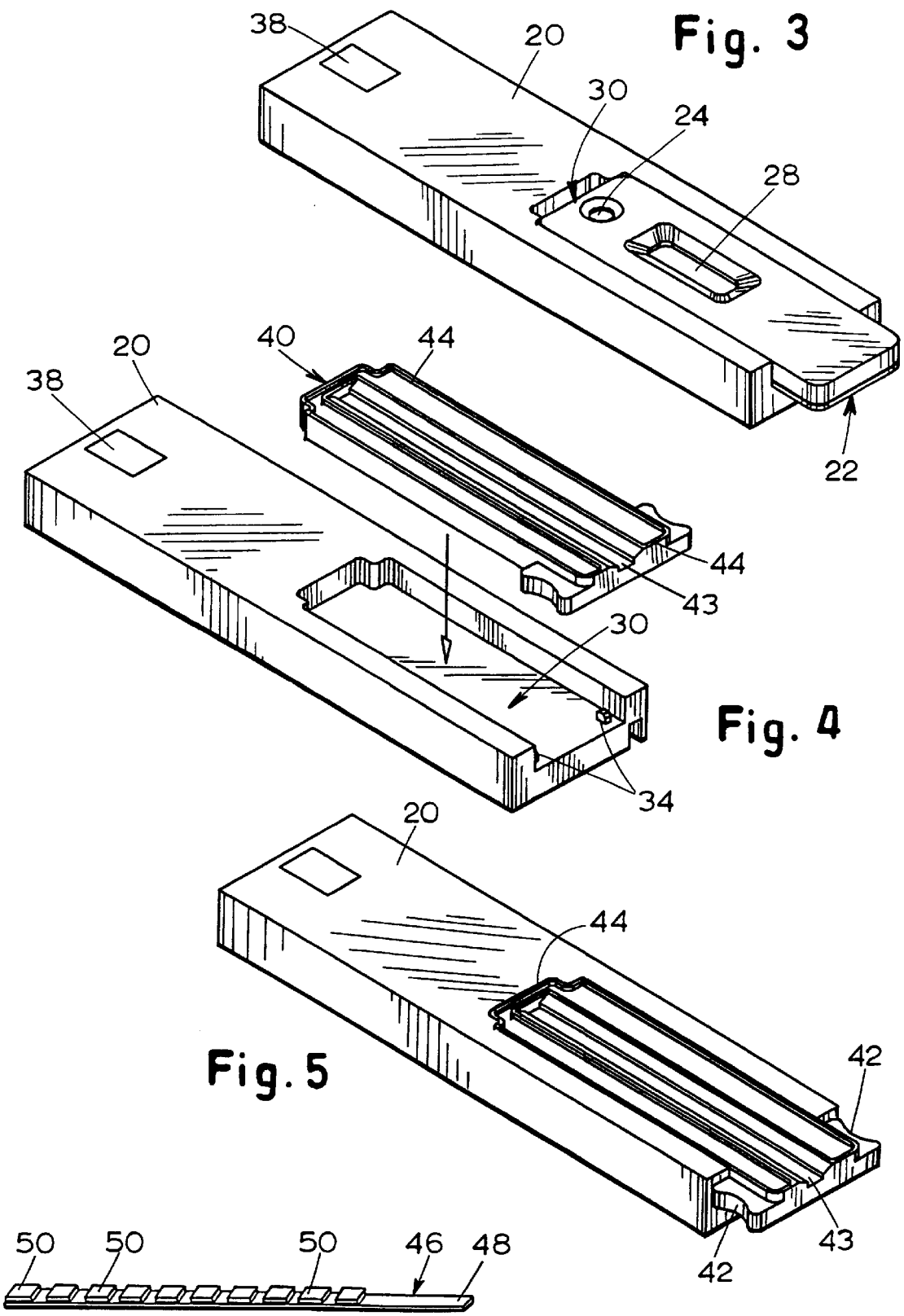

OPTICAL INSPECTION APPARATUS WITH REMOVABLE INSERTS

BACKGROUND OF THE INVENTION

The present invention relates to an apparatus and method for performing tests on a sample of body fluid to be optically inspected.

It is useful for various medical diagnostic purposes to utilize a reflectance spectroscope to analyze samples of body fluid, for example, to determine the color of a person's urine. A conventional spectroscope may determine the color of a urine sample disposed on a white, non-reactive pad by illuminating the pad and taking a number of reflectance readings from the pad, each having a magnitude relating to a different wavelength of visible light. The color of the urine on the pad may then be determined based upon the relative magnitudes of red, green, blue and infrared reflectance signals.

Conventional spectroscopes may be used to perform a number of different urinalysis tests utilizing a reagent strip on which a number of different reagent pads are disposed. Each reagent pad may be provided with a different reagent which causes a color change in response to the presence of a certain type of constituent in urine, such as leukocytes (white blood cells) or red blood cells. Such a reagent strip may have ten or more different types of reagent pads.

In a conventional spectroscope, the process of inspecting a reagent strip may be performed by dipping the reagent strip in a urine sample, blotting excess urine from the reagent strip, placing the reagent strip at a designated location in the spectrophotometer, and pressing a start button which causes the spectroscope to begin automatic processing and inspection of the reagent strip.

OBJECT

It is an object of the invention to overcome the disadvantages of the prior art. This object is solved by a combination of features of the main claim. The sub-claims disclose further advantageous embodiments of the invention.

SUMMARY OF THE INVENTION

The summary of the invention does not necessarily describe all necessary features of the invention, and the invention may also reside in a sub-combination of described features. The "Summary of the Invention," thus incorporated, presents, therefore, only an example, but not a limitation of the subject matter.

The invention is directed to an apparatus and method which allow different types of liquid carriers to be utilized in an optical inspection apparatus in a simple and convenient manner.

An apparatus in accordance with the invention is directed to an optical inspection apparatus adapted to inspect a liquid sample, such as a body fluid sample. The apparatus includes a tray that is adapted to be physically coupled to a first liquid sample carrier and a second liquid sample carrier, each of the first and second liquid sample carriers being adapted to hold a liquid sample. The first liquid sample carrier is of a first type and the second liquid sample carrier is of a second type different from the first type. The apparatus has a light source adapted to illuminate one of the liquid samples associated with one of the liquid sample carriers when the liquid sample carrier is coupled to the tray at an inspection location and a detector adapted to receive light from the liquid sample when the liquid sample is being illuminated by the light source.

The first liquid sample carrier may be in the form of a disposable reagent cassette, and the second liquid sample carrier may be adapted to support a reagent strip having a plurality of reagent pads disposed thereon, with the first liquid sample carrier having an elongated channel formed therein, the channel being sized to accommodate the reagent strip.

The invention is also directed to a method of using an optical inspection apparatus having a support tray that supports a liquid sample to be inspected, a light source that illuminates the liquid sample supported by the support tray when the support tray is at an inspection location, and a detector that detects light received from the liquid sample.

The method includes the steps of (a) placing onto the support tray a removable insert of a first type that carries a liquid sample, (b) causing the liquid sample to be illuminated by the light source, (c) causing light received from the liquid sample to be detected by the detector, (d) taking the removable insert off of the support tray, (e) placing onto the support tray a removable insert of a second type that carries a liquid sample, the second type of removable insert having a different physical structure from the first type of removable insert, (f) causing the liquid sample on the second type of removable insert to be illuminated by the light source, and (g) causing light received from the liquid sample to be detected by the detector.

The features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 3 is a perspective view of the support tray shown in FIG. 2 with the reagent cassette shown in the support tray;

FIG. 4 is a perspective view of the support tray of the spectroscope and a reagent strip holder that may be inserted into the support tray;

FIG. 5 is a perspective view of the support tray shown in FIG. 2 with the reagent strip holder shown in the support tray;

FIG. 6 is a perspective view of a reagent strip usable with the reagent strip holder of FIG. 5.

DETAILED DESCRIPTION OF THE PREFERRED EMBODIMENTS

Figure 1:
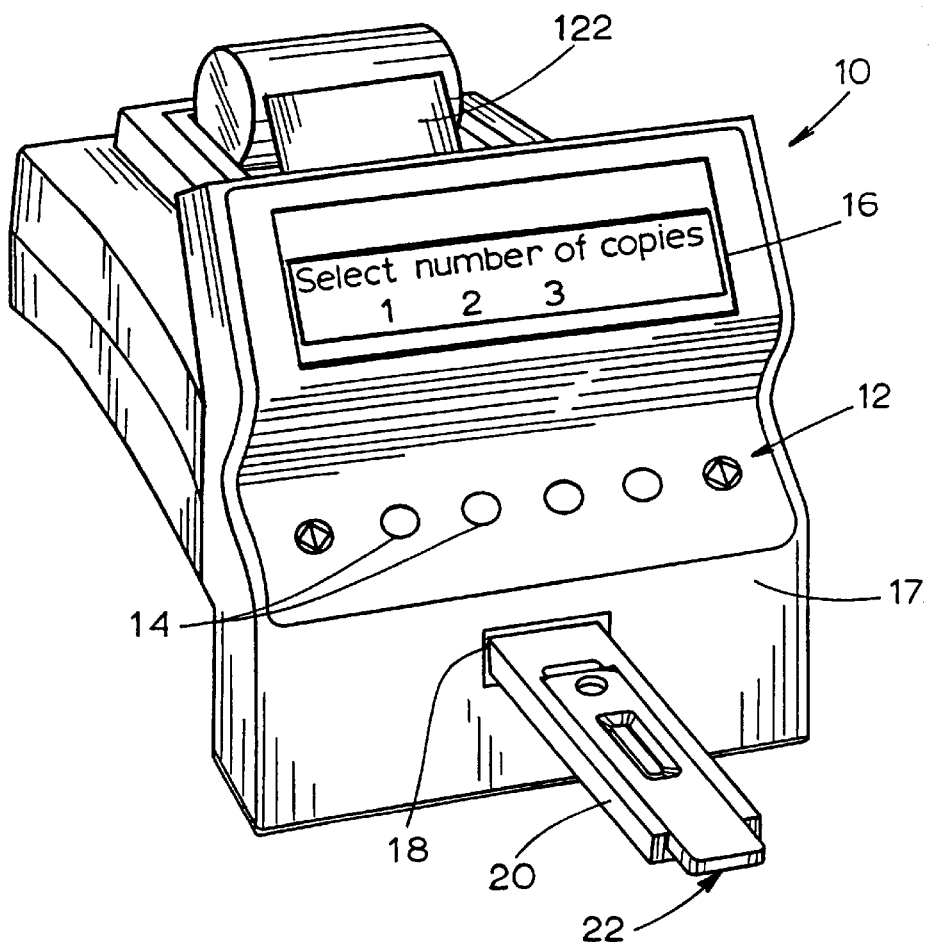
FIG. 1 is a perspective view of an optical inspection apparatus which may be used to perform various tests of a body fluid sample.

FIG. 1 illustrates an inspection apparatus 10, such as a reflectance spectroscope, for optically inspecting liquid samples such as body fluid samples. Referring to FIG. 1, the inspection apparatus 10 has an integral keyboard 12 with, a number of entry keys 14 that may be depressed by the user. A visual display 16 for displaying various messages relating to the operation of the inspection apparatus 10 is disposed above the keyboard 12.

Figure 2:
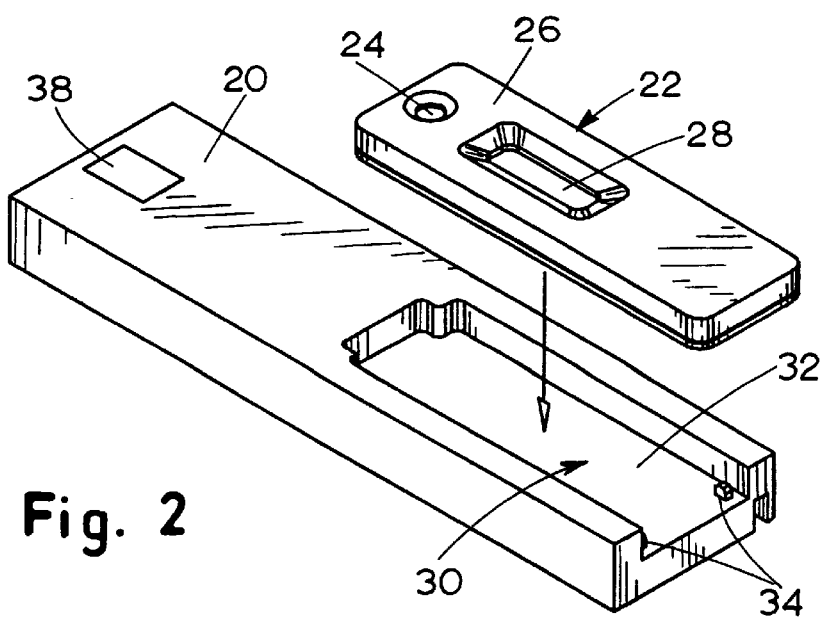
FIG. 2 is a perspective view of a support tray of the apparatus and a reagent cassette that may be inserted into the support tray.

The inspection apparatus 10 has a housing 17 with an opening 18 formed therein into which a support tray 20 may be retracted. Referring to FIGS. 1 and 2, the support tray 20 is adapted to receive a first type of liquid carrier or removable insert, which may be in the form of a reagent cassette 22. The reagent cassette 22 may be a disposable, single-use cassette for doing a pregnancy test, for example, in a conventional manner. The reagent cassette 22 has an opening or well 24 formed in an upper surface 26 into which a body fluid sample, such as urine, is placed. The interior of the reagent cassette 22 has a reagent strip (not shown) which may react with the body fluid sample placed in the well 24. Depending on the results of the test, the reagent strip may change color (e.g. a colored stripe may appear), which is determinable from viewing the reagent strip through a window 28 formed in the upper surface 26 of the reagent cassette 22.

As shown in FIG. 2, the support tray 20 has a rectangular recess 30 formed therein. The recess 30 is sized so that the reagent cassette 22 may be placed therein. As shown in FIGS. 1 and 3, the reagent cassette 22 is longer than the recess 30 so that when the reagent cassette 22 is placed within the recess 30, a portion of the reagent cassette 22 extends outwardly beyond the end of the support tray 20 in order to enable a user to grasp the outwardly extending end of the reagent cassette 22 and lift it out of the recess 30.

Referring to FIG. 2, an upper surface 32 of the recess 30 has a plurality of upwardly extending locating members 34, which may be in the form of pins, for example. When the reagent cassette 22 is placed within the support table 20, the locating members 34 are positioned within a plurality of apertures or holes formed in the bottom surface of the reagent cassette 22. When they are so positioned, the locating members 34 prevent the reagent cassette 22 from inadvertently sliding out of the recess 30. The support tray 20 may have a conventional calibration chip 38 of a certain color, such as white, disposed in its upper surface to facilitate calibration in a conventional manner.

Referring to FIGS. 4 and 5, the support tray 20 is adapted to receive a second type of liquid carrier or removable insert, which may be in the form of a reagent strip holder 40. The outer dimensions of the reagent strip holder 40 are generally the same as the outer dimensions of the reagent cassette 22 so that the reagent strip holder 40 also fits within the recess 30. The reagent strip holder 40 has a plurality of apertures or holes formed in its bottom surface which are positioned to receive the locating members 34 to prevent the reagent strip holder 40 from inadvertently sliding out of the recess 30, as described above in connection with the reagent cassette 22.

As shown in FIG. 5, the reagent strip holder 40 is longer than the recess 30 so that when the reagent strip holder 40 is placed within the recess 30, a portion of the reagent strip holder 40 extends outwardly beyond the end of the support tray 20 in order to enable a user to grasp the outwardly extending end of the reagent strip holder 40 and lift it out of the recess 30. The reagent strip holder 40 (and the reagent strip cassette 22) may be provided with a pair of arcuate curved portions 42 that act as finger grips to facilitate gripping the end of the reagent strip holder 40.

The reagent strip holder 40 has a central channel 43 formed therein which is sized to conform to the shape of a reagent strip 46 (FIG. 6). The reagent strip holder 40 may have a raised lip 44 which is disposed around The periphery of the reagent strip holder 40 to reduce the likelihood of body fluid samples contaminating the support tray 20.

Referring to FIG. 6, the reagent strip 46 may have a thin, non-reactive substrate 48 on which a number of reagent pads 50 are fixed. Each reagent pad 50 may be composed of a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color over a time period, depending on the reagent used and the characteristics of the urine sample. The reagent strip 46 may be, for example, a Multistix® reagent strip commercially available from Bayer Corporation.

Figure 7:
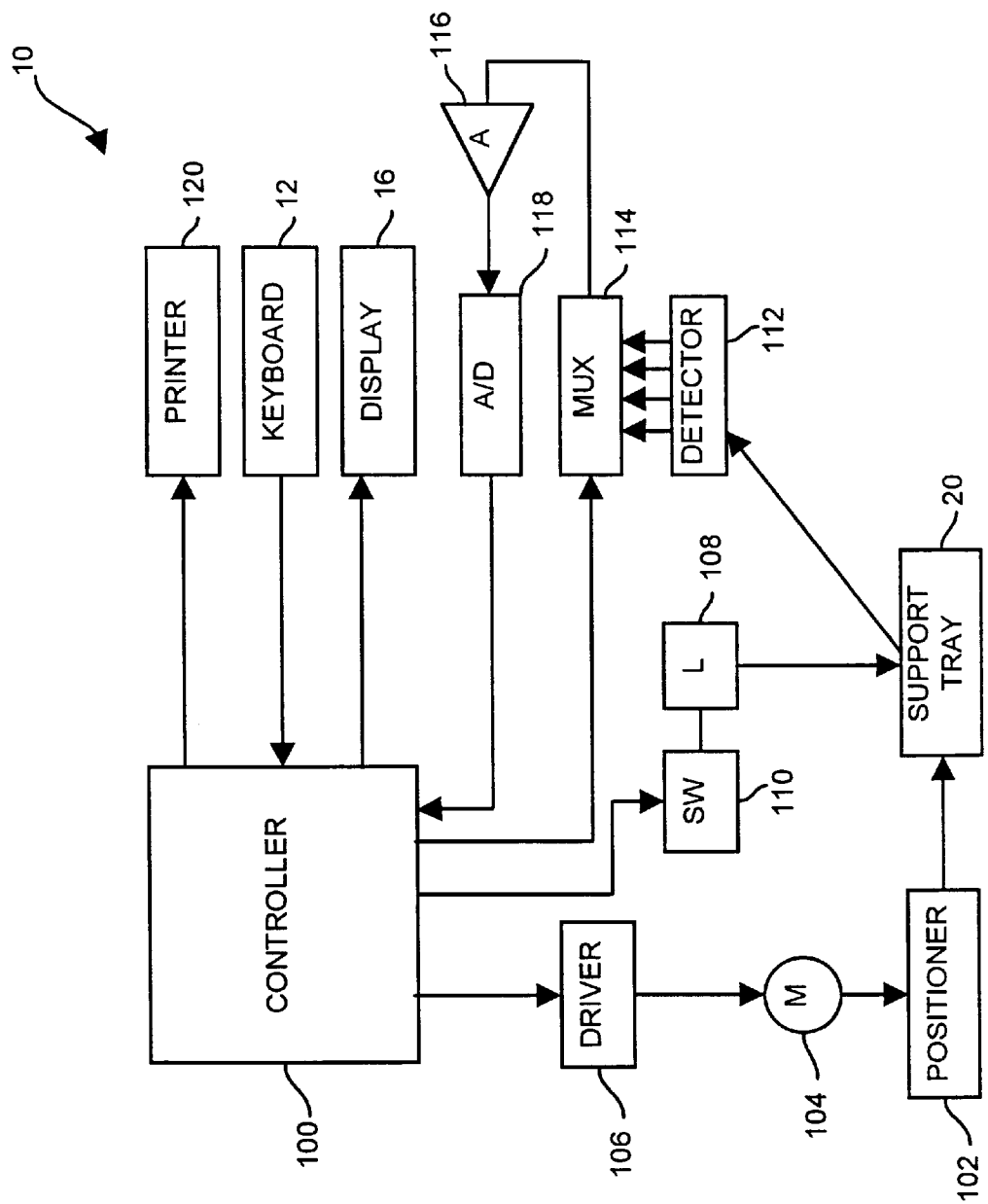
FIG. 7 is a block diagram of the electronics and other components of the apparatus of FIG. 1.

FIG. 7 is a block diagram of the electronics and other components of the inspection apparatus 10. Referring to FIG. 7, the operation of the inspection apparatus 10 is controlled by a controller 100. The controller 100 controls the movement of the support tray 20 between an outwardly extended position as shown in FIG. 1 and an optical inspection position in which the tray 20 is retracted inwardly into the housing 17 of the inspection apparatus 10. That movement is controlled by a conventional positioner 102 mechanically coupled to the tray 20 and a motor 104, such as a stepping motor, that is driven by drive signals generated by a driver circuit 106 connected to the controller 100.

When the support tray 20 is disposed so that either the reagent cassette 22 or the reagent strip holder 40 is disposed at an inspection location within the inspection apparatus 10, the controller 100 turns on a light source 108, which may be a light bulb or a light-emitting diode for example, via a switch 110 connected to the controller 100. The light source 108 may be turned on a period of time prior to the performance of an optical inspection so that it will be sufficiently warmed up. If the light source 108 is not needed to provide illumination within a period of time following a test, it may be turned off to conserve its life.

When the fluid sample in either the reagent cassette 22 or on the reagent strip holder 40 is illuminated by the light source 108, a detection apparatus 112 is used to detect light from the fluid sample. The detection apparatus 112 may be composed, for example, of a number of detectors disposed in a detector array, with each of the detectors generating a respective electrical reflectance signal which may be provided to a routing circuit in the form of a multiplexer 114, for example.

Each reflectance signal has a magnitude that depends on the amount of light detected by the associated detector. The controller 100 can selectively read any one of the reflectance signals by transmitting a select signal to the multiplexer 114. The multiplexer 114 then transmits the selected reflectance signal to an amplifier 116 and an analog-to-digital (A/D) converter 118, which transmits the binary signal corresponding to the analog reflectance signal output by the amplifier 116 to the controller 100.

The inspection apparatus 10 may be used to optically inspect multiple reagent cassettes 22 and multiple reagent strips 46 in any order desired by the user, since the reagent cassettes 22 and the reagent strip holder 40 have the same outer dimensions and fit within the recess 30 in the support tray 20.

In using the inspection apparatus 10, the user may prepare a reagent cassette 22 for optical inspection by putting a body fluid sample in the well 24 and then placing the cassette 22 in the recess 30 formed in the support tray 20. The user may then press a start button 14 on the keyboard 12 to cause the controller 100 to retract the support tray 20 inwardly so that the window 28 in the reagent cassette 22 is illuminated by the light source 108 and so that one or more reflectance signals are generated by the detection apparatus 112. After the reflectance signals are generated and processed by the controller 100, the test results may be displayed on the display 16 (FIG. 1) and/or printed out by a printer 120 (FIG. 7) onto a strip of paper 122 (FIG. 1).

In order to then perform one or more optical inspection tests on a reagent strip 46, the user would remove the reagent cassette 22 from the recess 30 in the support tray, discard the cassette 22, and place the reagent strip holder 40 in the recess 30 in the support tray 20.

To prepare a reagent strip 46 for optical inspection, the user would dip the reagent strip 46 into a body fluid sample to be tested so that the reagent pads 50 are immersed in the sample or otherwise apply the sample to the pads 50. After the side of the reagent strip 46 is blotted to remove excess fluid, the user places the strip 46 in the central channel 43 of the holder 40 and presses the start key 14 to initiate optical inspection of the reagent strip 46. The reagent strip holder 40 is then automatically retracted into the housing 17 and may be successively positioned at multiple locations within the inspection apparatus 10 so that each of the reagent pads 50 is optically inspected at an inspection location.

The provision of a support table 20 which is adapted to be used with different types of liquid carriers allows the user to quickly and conveniently change the liquid carrier while allowing the inspection apparatus to optically inspect different types of liquid-carrying mechanisms. It should be noted that the support tray 20 does not have to be removed from the inspection apparatus 10 in order to replace one type of liquid carrier with another type of liquid carrier.

Modifications of the inspection apparatus 10 will be apparent to those of ordinary skill in the art. For example, instead of providing the support tray 20 with the recess 30, the support tray 20 could be adapted to be physically coupled to each of the liquid carriers 22, 40 in alternative ways.

Numerous further modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed and sought to be secured by Letters Patent is:

1. An apparatus adapted to inspect a liquid sample, said apparatus comprising:
   a support tray (20) that is adapted to support a first insert (22) and a second insert (40), each of said first and second inserts (22, 40) being removable from said support tray (20), each of said first and second removable inserts (22, 40) being adapted to hold a liquid sample, said first removable insert (22) being of a first type and said second removable insert (40) being of a second type different from said first type;
   a light source (108) adapted to illuminate one of said liquid samples associated with one of said removable inserts(22 or 40) when said one removable insert (22 or 40) is supported by said support tray (20) at an inspection location; and
   a detector (112) adapted to receive light from said one liquid sample when said one liquid sample is being illuminated by said light source (108).

2. An apparatus as defined in claim 1 wherein said first liquid sample carrier (22) comprises a reagent cassette.

3. An apparatus as defined in claim 1 wherein said second removable insert (40) is adapted to support a reagent strip (46) having a plurality of reagent pads (50) disposed thereon.

4. An apparatus as defined in claim 3 wherein said second removable insert (40) has an elongated channel (43) formed therein, said channel (43) being sized to accommodate said reagent strip (46).

5. An apparatus as defined in claim 1 wherein said apparatus additionally comprises a housing (17) and wherein said support tray (20) is movable relative to said housing (17).

6. An apparatus as defined in claim 1 wherein said apparatus additionally comprises a housing and wherein said support tray (20) is retractable into said housing.

7. An apparatus as defined in claim 1 wherein said support tray (20) has a recess formed therein, wherein at least a portion of said first removable insert (22) is sized to fit within said recess (30), and wherein at least a portion of said second removable insert (40) is sized to fit within said recess (30).

8. An apparatus as defined in claim 7 wherein a locating member (34) is disposed within said recess (30), wherein each of said removable inserts (22, 40) has a hole formed therein which is sized to receive said locating member (34), and wherein said locating member (34) prevents said removable inserts (22, 40) from being slid outwardly from said support tray (20) and accurately positions said inserts (22, 40).

9. An apparatus as defined in claim 1 wherein a portion of each of said removable inserts (22, 40) extends outwardly beyond an outer end of said support tray (20).

10. An apparatus adapted to inspect a liquid sample, said apparatus comprising:
    a tray (20) that is adapted to be physically coupled to a first liquid sample carrier (22) and a second liquid sample carrier (40), each of said first and second liquid sample carriers (22, 40) being adapted to hold a liquid sample, said first liquid sample carrier (22) being of a first type and said second liquid sample carrier (40) being of a second type different from said first type;
    a light source (108) adapted to illuminate one of said liquid samples associated with one of said liquid sample carriers (22 or 40) when said one liquid sample carrier (22 or 40) is coupled to said tray (20) at an inspection location; and
    a detector (112) adapted to receive light from said one liquid sample when said one liquid sample is being illuminated by said light source (108).

11. An apparatus as defined in claim 10 wherein said first liquid sample carrier (22) comprises a reagent cassette.

12. An apparatus as defined in claim 10 wherein said second liquid sample carrier (40) is adapted to support a reagent strip (46) having a plurality of reagent pads (50) disposed thereon.

13. An apparatus as defined in claim 12 wherein said second liquid sample carrier (40) has an elongate channel (43) formed therein, said channel (43) being sized to accommodate said reagent strip (46).

14. A method of using an optical inspection apparatus (10) having a support tray (20) that supports a liquid sample to be inspected, a light source (108) that illuminates said liquid sample supported by said support tray (20) when said support tray (20) is at an inspection location, and a detector (112) that detects light received from said liquid sample, said method comprising the steps of:

(a) placing onto said support tray (20) a removable insert (22) of a first type that carries a liquid sample;

(b) causing said liquid sample of said step (a) to be illuminated by said light source (108);

(c) causing light received from said liquid sample of said step (a) to be detected by said detector (112);

(d) taking said removable insert (22) off of said support tray (20) after said step (c);

(e) placing onto said support tray (20) a removable insert (40) of a second type that carries a liquid sample, said removable insert (40) of said step (e) having a different physical structure from said removable insert (22) of said step (a);

(f) causing said liquid sample of said step (e) to be illuminated by said light source (108); and (g) causing light received from said liquid sample of said step (e) to be detected by said detector (112).

15. A method as defined in claim 14 wherein said step (a) comprises the step of placing said removable insert (22) into a recess formed (30) in said support tray (20).

16. A method as defined in claim 14 additionally comprising the step of (h) causing said support tray (20) to be retracted into a housing (17) of said inspection apparatus (10), said step (h) being performed after said step (a) and prior to said step (b).

17. A method as defined in claim 14 wherein said steps (d) and (e) are performed without removing said support tray (20) from said inspection apparatus (10).

* * * * *

UNITED STATES PATENT AND TRADEMARK OFFICE
CERTIFICATE OF CORRECTION

PATENT NO.    : 6,239,445 B1
DATED         : May 29, 2001
INVENTOR(S)   : Nazeer Shareef It is certified that error appears in the above-identified patent and that said Letters Patent is hereby corrected as shown below:

<u>Title page,</u>
Item [12], delete "Shaeef" and insert -- Shareef --.
Item [75], delete "Shaeef" and insert -- Shareef --.

Signed and Sealed this

Seventeenth Day of September, 2002

Attest:

Attesting Officer

JAMES E. ROGAN
*Director of the United States Patent and Trademark Office*